(12) United States Patent
Kim et al.

(10) Patent No.: US 10,781,285 B2
(45) Date of Patent: Sep. 22, 2020

(54) METHOD FOR PREPARING POLYETHYLENE GLYCOL DIALDEHYDE DERIVATIVE

(71) Applicant: Hanmi Fine Chemical Co., Ltd., Gyeonggi-do (KR)

(72) Inventors: Yu Rim Kim, Seoul (KR); Eun Rang Park, Gyeonggi-do (KR); Bo Sung Kwon, Gyeonggi-do (KR); Young Bum Cho, Gyeonggi-do (KR); Jun Ho Chu, Gyeonggi-do (KR)

(73) Assignee: Hanmi Fine Chemical Co., Ltd. (KR)

( * ) Notice: Subject to any disclaimer, the term of this patent is extended or adjusted under 35 U.S.C. 154(b) by 114 days.

(21) Appl. No.: 16/074,592

(22) PCT Filed: Feb. 21, 2017

(86) PCT No.: PCT/KR2017/001906
§ 371 (c)(1),
(2) Date: Aug. 1, 2018

(87) PCT Pub. No.: WO2017/146443
PCT Pub. Date: Aug. 31, 2017

(65) Prior Publication Data
US 2019/0040196 A1    Feb. 7, 2019

(30) Foreign Application Priority Data
Feb. 26, 2016 (KR) .................. 10-2016-0023217

(51) Int. Cl.
*C08G 65/331*    (2006.01)
*A61K 31/11*    (2006.01)
*A61K 47/60*    (2017.01)
*C08G 65/334*    (2006.01)
*C08G 65/48*    (2006.01)
*C08K 5/07*    (2006.01)

(52) U.S. Cl.
CPC ............ *C08G 65/331* (2013.01); *A61K 31/11* (2013.01); *A61K 47/60* (2017.08); *C08G 65/3312* (2013.01); *C08G 65/3346* (2013.01); *C08G 65/48* (2013.01); *C08K 5/07* (2013.01)

(58) Field of Classification Search
CPC .. C08G 65/331; C08G 65/48; C08G 65/3346; C08G 65/3312; A61K 47/60; A61K 31/11; C08K 5/07
See application file for complete search history.

(56) References Cited

U.S. PATENT DOCUMENTS

| | | | |
|---|---|---|---|
| 4,002,531 A | 1/1977 | Royer | |
| 5,252,714 A | 10/1993 | Harris et al. | |
| 6,465,694 B1 | 10/2002 | Baudys et al. | |
| 2006/0115450 A1* | 6/2006 | Nakamoto | C08G 65/2609 424/78.38 |
| 2007/0167606 A1 | 7/2007 | Won | |
| 2011/0071262 A1 | 3/2011 | Park et al. | |
| 2012/0077988 A1 | 3/2012 | Yamamoto et al. | |
| 2015/0073155 A1 | 3/2015 | Yoshioka et al. | |

FOREIGN PATENT DOCUMENTS

| | | |
|---|---|---|
| CA | 2803556 A1 | 12/2011 |
| CN | 1374875 A | 10/2002 |
| CN | 102985462 A | 3/2013 |
| CN | 103834002 A | 6/2014 |
| CN | 104245791 A | 12/2014 |
| EP | 2116561 A1 | 11/2009 |
| EP | 2586811 A1 | 5/2013 |
| KR | 100967833 B1 | 7/2010 |
| WO | 0126692 A1 | 4/2001 |

OTHER PUBLICATIONS

Search report from International Application No. PCT/KR2017/001906, dated Jun. 12, 2017.
Extended European Search Report including Written Opinion for Application No. EP17756781.5 dated Feb. 4, 2019.
J. Milton Harris et al: "Synthesis and characterization of poly(ethylwnw glycol) derivatives", Journal of Polymer Science, Polymer Chemistry Edition., Feb. 1, 1984, vol. 22, No. 2, XP055547265.
Search Report from Chinese Office Action for Application No. 201780012402.5 dated Jul. 3, 2020; 3 pages.

* cited by examiner

*Primary Examiner* — Shane Fang
(74) *Attorney, Agent, or Firm* — Lerner, David, Littenberg, Krumholz & Mentlik, LLP

(57) ABSTRACT

The present invention relates to an improved method for preparing a high purity polyethylene glycol dialdehyde derivative. The preparation method can provide the polyethylene glycol dialdehyde derivative suitable as a raw material for pharmaceuticals because of high purity and terminal activity, by using PEG-diacetal, which is prepared by reacting polyethyleneglycol methanesulfonate with dialkoxy-1-propanol, as an intermediate.

15 Claims, No Drawings

METHOD FOR PREPARING POLYETHYLENE GLYCOL DIALDEHYDE DERIVATIVE

CROSS-REFERENCE TO RELATED APPLICATIONS

This application is a national phase entry under 35 U.S.C. § 371 of International Application No. PCT/KR2017/001906, filed Feb. 21, 2017 which claims priority to Korean Patent Application No. 10-2016-0023217, filed Feb. 26, 2016, the disclosures of which are incorporated herein by reference.

TECHNICAL FIELD

The present invention relates to an improved method for preparing high purity polyethylene glycol dialdehyde derivatives.

BACKGROUND ART

Polyethylene glycol (PEG) is one of the polymers that have strong hydrophilicity and effectively makes hydrogen bonds with water molecules. PEG can be applied to the development of pharmaceuticals in various ways because it has excellent solubility in various organic solvents other than water and has little toxicity. For example, PEG may bind properly with proteins and enzymes to reduce drug toxicity, and may increase the solubility of an insoluble drug and thus may control activity and half-life thereof to form a PEG-drug complex having desired properties.

In order to bind PEG with a drug, a PEG derivative in which various functional groups are introduced into the hydroxyl group (OH group) at the terminal of the PEG chain is used. Examples of such PEG derivatives include PEG-aldehyde, PEG-acetaldehyde, PEG-propionaldehyde and the like. The aldehyde group at the ends of these derivatives can selectively react with the amino terminal of the protein.

Several methods for introducing such reactive aldehyde groups into the terminals of the PEG chain are known. U.S. Pat. No. 6,465,694 discloses a method of reacting the terminals of PEG with oxygen under a catalyst to oxidize the terminal hydroxyl group of PEG to an aldehyde group. However, the method using such an oxidation reaction has a problem that the PEG chain can be decomposed. In addition, when the aldehyde group is prepared through hydrolysis and oxidation reaction after introduction of an acetal group into the terminals of PEG, because the raw materials used are expensive, there are difficulties in commercialization.

U.S. Pat. No. 5,252,714 discloses a method for preparing PEG-propionaldehyde by reacting PEG with 3-chlorodiethylacetalpropion-aldehyde and then hydrolyzing under acidic conditions.

In addition, U.S. Pat. No. 4,002,531 discloses a pegylation reaction (or PEGylation) for introducing PEG into a drug wherein mPEG(methoxy-PEG) is oxidized to produce mPEG-acetaldehyde, and then by using it, the trypsin enzyme is pegylated to be used in a drug delivery system. However, in such an oxidation reaction, the PEG chain may be decomposed to increase the distribution, and the reaction conversion rate may be lowered to 80% or less.

Therefore, the inventors of the present invention have studied a method for producing a polyethylene glycol dialdehyde derivative more safely and efficiently, and as a result, found that when using PEG-diacetal as an intermediate, the high purity polyethylene glycol dialdehyde derivative can be prepared, thereby completing the present invention.

PRIOR ART LITERATURE

Patent Literature

U.S. Pat. No. 6,465,694 (Oct. 15, 2002), Method for preparation of polyethylene glycol aldehyde derivatives
U.S. Pat. No. 5,252,714 (Oct. 12, 1993), Preparation and use of polyethylene glycol propionaldehyde
U.S. Pat. No. 4,002,531 (Jan. 11, 1977), Modifying enzymes with polyethylene glycol and product produced thereby

DISCLOSURE

Technical Problem

Accordingly, it is an object of the present invention to provide a method for safely and efficiently preparing a high-purity polyethylene glycol dialdehyde derivative having a high terminal activity.

Technical Solution

In order to achieve the above object, the present invention provides a method for preparing a polyethylene glycol dialdehyde derivative represented by the following formula 4, comprising 1) subjecting a compound of the following formula 2 to an activation treatment with a metal base and then subjecting it to a pegylation with a compound of the following formula 1 to prepare a compound of the following formula 3; and 2) subjecting the compound of formula 3 to an acid treatment:

(Formula 1)

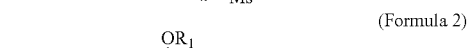

(Formula 2)

(Formula 3)

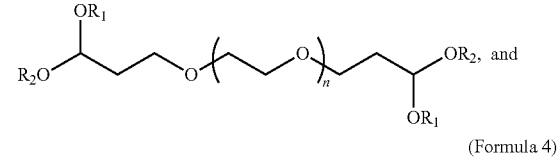

(Formula 4)

wherein Ms is methanesulfonyl, $R_1$ and $R_2$ are the same or different from each other and each independently represents a (C1-C9) alkyl group, and n is an integer of 3 to 2000.

Advantageous Effects

The preparation method according to the present invention has an advantage in that it is suitable for mass production because it does not require a separation process (purification process) such as column chromatography, and it can provide a polyethylene glycol dialdehyde derivative suitable as a raw material for pharmaceuticals because of high purity and terminal activity.

Best Mode

The method for preparing the polyethylene glycol dialdehyde derivative (hereinafter, referred to as 'PEG-dialdehyde') comprises 1) subjecting the compound of formula 2 to the activation treatment in the presence of the metal base in a solvent and then subjecting it to the pegylation with the compound of formula 1 to prepare the compound of formula 3; and 2) subjecting the compound of formula 3 to the acid treatment in a solvent to prepare the compound of formula 4.

The preparation method of the present invention will be described in more detail as follows:

In step 1), as shown in Reaction Scheme 1 below, the compound of formula 2 (dialkoxy-1-propanol) is activated, and thereafter is subjected to pegylation with the compound of formula 1 (PEG-Ms) to form the compound of formula 3 (PEG-diacetal).

[Reaction Scheme 1]

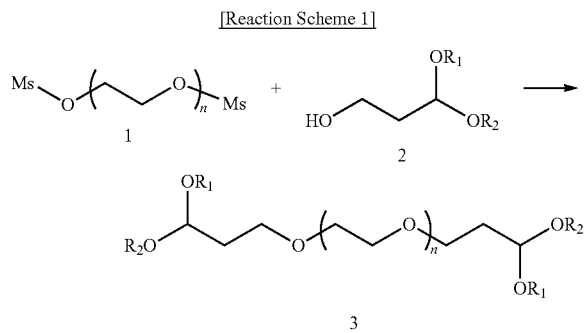

wherein Ms is methanesulfonyl, $R_1$ and $R_2$ are the same or different from each other and each independently represents a (C1-C9) alkyl group, and n is an integer of 3 to 2000.

The alkyl group of $R_1$ and $R_2$ is a linear or branched alkyl group, such as methyl, ethyl, propyl, isopropyl, butyl, isobutyl, hexyl, heptyl, octyl, or nonyl, and preferably C1-C4, and more preferably methyl, ethyl, propyl, isopropyl or butyl, and most preferably ethyl.

n is directly related to the molecular weight of the polyethylene glycol(PEG) to be finally produced, and may be an integer of 3 to 2000.

As a specific example, in step 1), the compound of formula 2 (dialkoxy-1-propanol) is added to the solvent under an inert gas atmosphere or in an inert atmosphere in which an inert gas is continuously introduced, and is activated by stirring after the addition of the metal base, and thereafter is subjected to pegylation with the compound of formula 1 (PEG-Ms) to prepare the compound of formula 3 (PEG-diacetal) in a solution state.

The reaction of step 1) may be carried out (i) under an inert gas atmosphere in which the gas inside the reactor is replaced by an inert gas, or (ii) under a state in which an inert gas is continuously introduced and thus the gas inside the reactor is replaced. In the case of (ii), for example, the flow rate of the inert gas may be 0.1 to 6.0 L/min, specifically 0.5 to 4.0 L/min, more specifically 0.5 to 2.0 L/min.

Here, the inert gas may be at least one selected from the group consisting of nitrogen, argon, and helium, preferably nitrogen.

The solvent used in the reaction of step 1) may be at least one selected from the group consisting of toluene, dichloromethane, chloroform, tetrahydrofuran, acetonitrile and 1,4-dioxane.

In addition, the metal base may be a metal alkoxide, a metal hydride, or a mixture thereof. The metal alkoxide may be at least one selected from the group consisting of sodium methoxide, sodium ethoxide, sodium t-butoxide, sodium t-pentoxide, potassium t-butoxide and potassium t-pentoxide. The metal hydride may be sodium hydride.

The metal base may be used in an amount of 1 to 10 equivalents based on 1 equivalent of the compound of formula 1 (PEG-Ms), preferably 3 to 7 equivalents.

Specific examples of the compound of formula 2 (dialkoxy-1-propanol) include dimethoxy-1-propanol, diethoxy-1-propanol, dipropoxy-1-propanol, dibutoxy-1-propanol, diisopropoxy-1-propanol and the like.

The compound of formula 2 may be used in an amount of 2 to 30 equivalents based on 1 equivalent of the compound of formula 1, preferably 5 to 15 equivalents.

The activation treatment of step 1) may be carried out at a temperature of 20° C. to 90° C., preferably 35° C. to 80° C. In addition, the pegylation in step 1) may be carried out at a temperature of 0° C. to 90° C., preferably 0° C. to 40° C.

In particular, the activation treatment and pegylation of this step 1) directly affect the terminal activity of PEG-dialdehyde. The term 'terminal activity' means that the aldehyde group, which is a functional group having an activity, exists at the terminal of PEG-dialdehyde. In that case, the higher the value of terminal activity, the higher the amount of dialdehyde present at the terminal of PEG. A terminal activity of 100% means that CHO binds to both terminals of PEG at 100%. In that case, the aldehyde group can selectively react with the amino terminal of the protein or peptide. Considering this, the term 'terminal activity' may be interpreted as the degree of pegylation that can be introduced into PEG-dialdehyde. Therefore, in order to use as a raw material for pharmaceuticals such as bio drugs, it is advantageous that a high proportion of aldehyde group is present at both terminals of PEG-dialdehyde.

The reaction of step 2) of the present invention described below is more rapid than step 1), is easy and can be achieved with a high conversion rate, and thus control of step 1) is important to ensure high terminal activity.

In this step 1), the PEG of formula 1 reacts with the compound of formula 2. In that case, the compound of formula 3 is prepared while increasing the reactivity between the compound of formula 1 and the compound of formula 2 by controlling the reaction parameter when activating the hydroxyl group of the compound of formula 2.

The parameters when performing the activation treatment include reaction temperature, time, molar ratio, etc. Among these various parameters, it is necessary to select the metal base and the atmosphere directly related to purity and yield and to control them.

As a result, any one or more of the above-mentioned ones may be used as a metal base, and preferably sodium t-pentoxide is used. In addition, it is preferable to perform under an inert gas atmosphere or in a state in which an inert gas is continuously introduced. When performing in air or oxygen atmosphere, the terminal activity of the final PEG-dialdehyde is greatly reduced. In addition, when the inert gas is introduced at the above-mentioned flow rate, the PEG-dialdehyde with improved terminal activity can be obtained.

On the other hand, a subsequent treatment process can be considered by the content related to the terminal activity.

The compound of formula 3 (PEG-diacetal) prepared after the pegylation in step 1) may be isolated in a solid phase by crystallization or the like or concentrated in an oil phase and then used in the next step. Alternatively, the compound of formula 3 may be prepared in the form of a solution by the reaction of step 1) and then may be used in situ in the subsequent step 2) without separation. That is, in the case of (ii) above, the reaction solution obtained in step 1) can be used in situ in the reaction of step 2) without separation. Preferably, when the compound of formula 3 is applied to the next step in the continuous use mode, the terminal activity was further improved.

In step 2) above, as shown in Reaction Scheme 2 below, the compound of formula 4 (PEG-dialdehyde) is prepared by reacting the compound of formula 3 (PEG-diacetal) prepared in the previous step 1) with an acid in a solvent.

[Reaction Scheme 2]

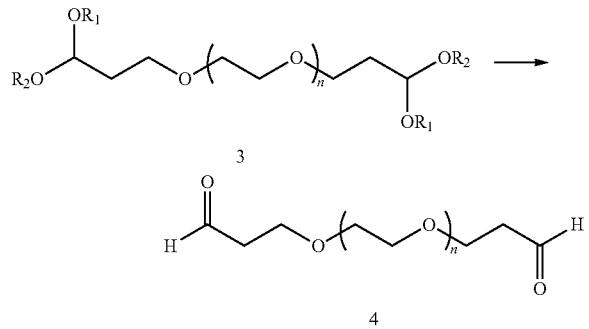

wherein $R_1$, $R_2$ and n are as described above.

As a specific example, in step 2), the compound of formula 3 (PEG-diacetal) obtained in the form of a solution by the reaction of the previous step 1) is added to an aqueous acid solution in a solvent and reacted, and then the solution obtained may be treated with an organic solvent to prepare the compound of formula 4 (PEG-dialdehyde).

The solvent used in the reaction of step 2) may be selected from the group consisting of water, methanol, ethanol, propanol, t-butanol and mixtures thereof. Preferably, the solvent used in the reaction of step 2) may comprise water.

In addition, the acid may be selected from the group consisting of hydrochloric acid, acetic acid, formic acid, trifluoroacetic acid, phosphoric acid and mixtures thereof.

The reaction of step 2) may be carried out at a temperature of 0° C. to 50° C., preferably 20° C. to 30° C.

The solution obtained through the reaction of step 2) may be further subjected to extraction using an organic solvent, concentration, crystallization and the like. The organic solvent may be selected from the group consisting of dichloromethane, chloroform, ethyl acetate and mixtures thereof.

Specifically, the organic solvent used in the extraction may be selected from the group consisting of dichloromethane, chloroform, ethyl acetate and mixtures thereof. In addition, the organic solvent used in the crystallization may be a mixture of (a) at least one solvent selected from the group consisting of dichloromethane, chloroform and ethyl acetate and (b) at least one solvent selected from the group consisting of hexane, heptane, diethyl ether and methyl t-butylether.

According to a preferred embodiment of the preparation method of the present invention, $R_1$ and $R_2$ in the compounds of formula 2 and formula 3 are the same and they may be ethyl. In that case, the reaction of step 1) above may be carried out under an inert gas atmosphere or in a state in which an inert gas is continuously introduced. The inert gas may be selected from the group consisting of nitrogen, argon, helium and mixtures thereof. In addition, the compound of formula 3 can be used in situ in the reaction of step 2) without separation after being prepared in a solution state by the reaction of step 1). In addition, the acid used in step 2) may be hydrochloric acid. In addition, the compound of formula 4 can be obtained by treating the solution obtained by the reaction of step 2) with an organic solvent. The organic solvent may be at least one selected from the group consisting of dichloromethane, chloroform and ethyl acetate.

Meanwhile, the compound of formula 1 (PEG-Ms) used as a starting material in step 1) of the present invention can be prepared, for example, through the route as shown in the following Reaction Scheme 3:

[Reaction Scheme 3]

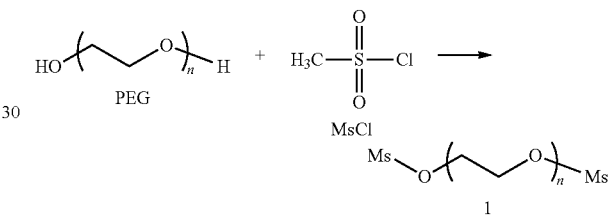

wherein Ms and n are as described above.

That is, the compound of formula 1 can be prepared by reacting polyethylene glycol(PEG) with methanesulfonyl chloride(MsCl) in the presence of base. Here, the base used in preparing the compound of formula 1 may be triethylamine, tributylamine, or a mixture thereof.

As described above, the production method of the present invention can produce PEG-dialdehyde with high purity in a stable and reproducible manner by proceeding the reaction while using, as a starting material, a compound in which methane sulfonyl chloride as a leaving group is introduced into PEG which has a stable structure. In addition, since the preparation method of the present invention does not require a separation process such as column chromatography, the preparation method does not preferably include a step of performing column chromatography and accordingly, has an advantage of being suitable and efficient for mass production and being capable of mass-producing products with high quality reproducibly.

In addition, according to the preparation method of the present invention, there is an advantage that since purity and terminal activity are high, a polyethylene glycol dialdehyde derivative suitable as a raw material for pharmaceuticals may be provided. Specifically, the polyethylene glycol dialdehyde derivative prepared according to the present invention has a terminal activity of 60% or more, preferably 70% or more, more preferably 80% or more.

Hereinafter, in order to facilitate understanding of the present invention, preferred embodiments will be described and explained. However, it will be apparent to those skilled in the art that the following examples are illustrative of the present invention, but that various changes and modifications can be made within the scope and spirit of the present invention.

[Evaluation]

The analysis of each material produced in the following Examples and Comparative Examples was evaluated based on the followings:

(1) Confirmation of structure: The measurement was carried out using a $^1$H-NMR apparatus.

(2) Number average molecular weight (Mn), polydispersity index (PDI), and main peak fraction (MPF): The number average molecular weight, PDI and MPF values of the binding resin were measured by gel permeation chromatography (GPC). The GPC was performed by a RI detector (refractive index detector) through size-exclusion chromatography column using high performance liquid chromatography (HPLC).

(3) Terminal activity: Terminal activity was analyzed by a RI detector (refractive index detector) through an ion exchange column using high performance liquid chromatography (HPLC).

Preparation Example 1: Preparation of PEG-Ms

Nitrogen gas was continuously introduced into the reaction vessel, and the reaction vessel was flame dried to remove moisture. 100 g of PEG (Mn, about 3.4 K) was added to the reaction vessel, 300 mL of dichloromethane was added and dissolved, and the solution was cooled to 5° C. 23.0 mL of triethylamine was added to the reaction solution, and 12.6 mL of methanesulfonyl chloride was added while maintaining the temperature at 5° C. The reaction solution was stirred at 5° C. for 2.5 hours, 300 mL of distilled water was added, and then the mixture was stirred for 10 minutes to separate an organic layer. To the aqueous layer, 300 mL of dichloromethane was added for further extraction, and then the organic layer was separated and combined. The organic layer was washed with 300 mL of distilled water, dried over anhydrous magnesium sulfate, filtered, and the filtrate was concentrated under reduced pressure. 100 mL of dichloromethane was added to the concentrate and dissolved it, and then, the solution obtained was added dropwise to 1500 mL of methyl t-butyl ether over 30 minutes, and the mixture was stirred at room temperature for 1 hour. The resulting solid was filtered, washed with methyl t-butyl ether, and then dried by nitrogen at room temperature to obtain 97 g (yield: 92.6%) of the target compound PEG-Ms. All the above reaction procedures were carried out under the condition that nitrogen gas was continuously introduced into the reaction vessel at a flow rate of 1.1 L/min.

$^1$H-NMR (CDCl$_3$, 400 MHz) δ4.36-4.34 (m, 4H), 3.72-3.44 (m, 304H), 3.05 (s, 6H).

The number average molecular weight (Mn) measured by GPC: 3505.

Polydispersity (PDI): 1.04.

MPF (main peak fraction) purity: 99.42%.

EXAMPLE 1

Preparation of PEG-dialdehyde

Step 1): Preparation of PEG-diethyl Acetal

Nitrogen gas was continuously introduced into two 500 mL reaction vessels, and these reaction vessels were flame dried to remove moisture.

To one of the reaction vessels, 1.8 mL of 3,3-diethoxy-1-propanol and 40 mL of toluene were charged. Thereafter, 1.4 g of potassium t-butoxide was added and the temperature was raised to 50° C., and the solution was activated by stirring for 1 hour and cooled to room temperature.

To the other reaction vessel, 10 g of PEG-Ms obtained in Preparation Example 1 and 40 mL of toluene were added, and the previously activated solution was added dropwise over 1 hour and then stirred at room temperature for 2 hours. 50 mL of an aqueous saturated ammonium chloride solution was added to the reaction solution, stirred for 5 minutes, and 100 mL of dichloromethane was added to extract the organic layer. 100 mL of dichloromethane was added to the aqueous layer, and the organic layer was further extracted, and the organic layers were combined and concentrated under reduced pressure. The concentrate was dissolved in 10 mL of dichloromethane, 150 mL of methyl t-butyl ether was added dropwise, and the mixture was stirred at room temperature for 2 hours. The resulting crystals were filtered, washed with methyl t-butyl ether, and dried by nitrogen at room temperature to obtain 9.3 g (yield: 90.0%) of the target compound PEG-diethyl acetal.

All the above reaction procedures were carried out under the condition that nitrogen gas was continuously introduced into the reaction vessel at a flow rate of 1.1 L/min.

Step 2): Preparation of PEG-dialdehyde

To another reaction vessel, 9 g of PEG-diethyl acetal obtained above was added and dissolved using 45 mL of distilled water, and then, 90 mL of 0.1N hydrochloric acid was added dropwise. The reaction solution was stirred at room temperature for 2 hours and then adjusted to pH 6 using 5% sodium bicarbonate solution. 90 mL of dichloromethane was added to the reaction solution to extract the organic layer, and 90 mL of dichloromethane was added to the aqueous layer to further extract the organic layer. The organic layers were combined, dried over sodium sulfate, filtered, and the filtrate was concentrated under reduced pressure. The concentrate was dissolved in 9 mL of dichloromethane, 180 mL of methyl t-butyl ether was added dropwise, and the mixture was stirred at room temperature for 2 hours. The resulting crystals were filtered, washed with methyl t-butyl ether, and dried by nitrogen at room temperature to obtain 8 g (yield: 92.0%) of the target compound PEG-dialdehyde.

Terminal activity: 66.8%.

$^1$H-NMR (CDCl$_3$, 400 MHz) δ9.49 (t, 2H, J=2 Hz), 3.59-3.83 (m, 304H), 2.66-2.70 (m, 4H), 1.89 (m, 4H).

EXAMPLE 2

Preparation of PEG-dialdehyde

Step 1): Preparation of PEG-diethyl Acetal

Nitrogen gas was continuously introduced into two 500 mL reaction vessels, and these reaction vessels were flame dried to remove moisture.

To one of the reaction vessels, 1.8 mL of 3,3-diethoxy-1-propanol and 40 mL of toluene were charged. Thereafter, 1.4 g of potassium t-butoxide was added and the temperature was raised to 50° C., and the solution was activated by stirring for 1 hour and cooled to room temperature.

To the other reaction vessel, 10 g of PEG-Ms obtained in Preparation Example 1 and 40 mL of toluene were added, and the previously activated solution was added dropwise over 1 hour and then stirred at room temperature for 2 hours. 50 mL of an aqueous saturated ammonium chloride solution was added to the reaction solution, stirred for 5 minutes, and 100 mL of dichloromethane was added to extract the organic layer. 100 mL of dichloromethane was added to the aqueous layer to further extract the organic layer, and the organic layers were combined and concentrated under reduced pressure.

All the above reaction procedures were carried out under the condition that nitrogen gas was continuously introduced into the reaction vessel at a flow rate of 1.1 L/min.

Step 2): Preparation of PEG-dialdehyde

To another reaction vessel, the concentrate obtained above was added and dissolved using 50 mL of distilled water, and then, 100 mL of 0.1N hydrochloric acid was added dropwise. The reaction solution was stirred at room temperature for 2 hours and then adjusted to pH 6 using 5% sodium bicarbonate solution. 100 mL of dichloromethane was added to the reaction solution to extract the organic layer, and 100 mL of dichloromethane was added to the aqueous layer to further extract the organic layer. The organic layers were combined, dried over anhydrous sodium sulfate, filtered, and the filtrate was concentrated under reduced pressure. The concentrate was dissolved in 8 mL of dichloromethane, 200 mL of methyl t-butyl ether was added dropwise, and the mixture was stirred at room temperature for 2 hours. The resulting crystals were filtered, washed with methyl t-butyl ether, and dried by nitrogen at room temperature to obtain 8.5 g of the target compound PEG-dialdehyde (yield: 86.0%).

Terminal activity: 73.1%.

EXAMPLE 3

Preparation of PEG-dialdehyde

Step 1): Preparation of PEG-diethyl Acetal

Nitrogen gas was continuously introduced into two 500 mL reaction vessels, and these reaction vessels were flame dried to remove moisture.

To one of the reaction vessels, 2.2 mL of 3,3-diethoxy-1-propanol and 40 mL of toluene were charged. Thereafter, 1.4 g of potassium t-butoxide was added and the temperature was raised to 50° C., and the solution was activated by stirring for 1 hour and cooled to room temperature.

To the other reaction vessel, 10 g of PEG-Ms obtained in Preparation Example 1 and 40 mL of toluene were added, and the previously activated solution was added dropwise over 1 hour and then stirred at room temperature for 2 hours. 30 mL of an aqueous saturated ammonium chloride solution was added to the reaction solution, stirred for 5 minutes, and 30 mL of dichloromethane was added to extract the organic layer.

All the above reaction procedures were carried out under the condition that nitrogen gas was continuously introduced into the reaction vessel at a flow rate of 1.1 L/min.

Step 2): Preparation of PEG-dialdehyde

To another reaction vessel, 200 mL of 0.05N hydrochloric acid was added, and the organic layer extracted above was added dropwise over 30 minutes. The reaction solution was stirred at room temperature for 1 hours and then adjusted to pH 6 using 5% sodium bicarbonate solution. 100 mL of dichloromethane was added to the reaction solution, and the organic layer was dried over anhydrous sodium sulfate, filtered, and the filtrate was concentrated under reduced pressure. The concentrate was dissolved in 8 mL of dichloromethane, 200 mL of methyl t-butyl ether was added dropwise, and the mixture was stirred at room temperature for 1 hours. The resulting crystals were filtered, washed with methyl t-butyl ether, and dried by nitrogen at room temperature to obtain 7.2 g (yield: 73.0%) of the target compound PEG-dialdehyde.

Terminal activity: 77.1%.

EXAMPLE 4

Preparation of PEG-dialdehyde

Step 1): Preparation of PEG-diethyl Acetal

Nitrogen gas was continuously introduced into two 500 mL reaction vessels, and these reaction vessels were flame dried to remove moisture.

To one of the reaction vessels, 2.2 mL of 3,3-diethoxy-1-propanol and 40 mL of toluene were charged. Thereafter, 1.4 g of sodium t-pentoxide was added and the temperature was raised to 50° C., and the solution was activated by stirring for 1 hour and cooled to room temperature.

To the other reaction vessel, 10 g of PEG-Ms obtained in Preparation Example 1 and 40 mL of toluene were added, and the previously activated solution was added dropwise over 1 hour and then stirred at room temperature for 2 hours. 30 mL of distilled water was added to the reaction solution, stirred for 10 minutes to extract the aqueous layer. 30 mL of dichloromethane and 80 mL of toluene were added to the aqueous layer and stirred for 10 minutes to extract the organic layer.

All the above reaction procedures were carried out under the condition that nitrogen gas was continuously introduced into the reaction vessel at a flow rate of 1.1 L/min.

Step 2): Preparation of PEG-dialdehyde

By repeating the same procedure as in step 2) of Example 3 above using the organic layer extracted in step 1) above, 4.7 g (yield: 48%) of the target compound PEG-dialdehyde was obtained.

Terminal activity: 82.6%.

EXAMPLE 5

Preparation of PEG-dialdehyde

Step 1): Preparation of PEG-diethyl Acetal

Nitrogen gas was continuously introduced into two 500 mL reaction vessels, and these reaction vessels were flame dried to remove moisture.

To one of the reaction vessels, 4.5 mL of 3,3-diethoxy-1-propanol and 40 mL of toluene were charged. Thereafter, 1.6 g of sodium t-pentoxide was added and the temperature was raised to 50° C., and the solution was activated by stirring for 1 hour and cooled to room temperature.

To the other reaction vessel, 10 g of PEG-Ms obtained in Preparation Example 1 and 40 mL of toluene were added, and the previously activated solution was added dropwise over 1 hour and then stirred at room temperature for 2 hours. 30 mL of distilled water was added to the reaction solution, stirred for 10 minutes to extract the aqueous layer. 30 mL of dichloromethane and 80 mL of toluene were added to the aqueous layer and stirred for 10 minutes to extract the organic layer.

All the above reaction procedures were carried out under the condition that nitrogen gas was continuously introduced into the reaction vessel at a flow rate of 1.1 L/min.

Step 2): Preparation of PEG-dialdehyde

By repeating the same procedure as in step 2) of Example 3 above using the organic layer extracted in step 1) above, 4.7 g (yield: 48%) of the target compound PEG-dialdehyde was obtained.

Terminal activity: 85.8%.

$^1$H-NMR (CDCl$_3$, 400 MHz) δ9.49 (t, 2H, J=2 Hz), 3.59-3.83 (m, 304H), 2.66-2.70 (m, 4H), 1.89 (m, 4H).

The number average molecular weight (Mn) measured by GPC: 3321.
Polydispersity(PDI): 1.04.
MPF (main peak fraction) purity: 99.51%.

EXAMPLE 6

Preparation of PEG-dialdehyde

Step 1): Preparation of PEG-diethyl Acetal

Nitrogen gas was continuously introduced into two 500 mL reaction vessels, and these reaction vessels were flame dried to remove moisture.

To one of the reaction vessels, 40 mL of toluene and 4.48 mL of 3,3-diethoxy-1-propanol were charged. Thereafter, 0.78 g of sodium methoxide was added and the temperature was raised to 50° C., and the solution was activated by stirring for 1 hour and cooled to room temperature.

To the other reaction vessel, 10 g of PEG-Ms obtained in Preparation Example 1 and 40 mL of toluene were added, and the previously activated solution was added dropwise over 1 hour and then stirred at room temperature for 2 hours. 30 mL of water was added to the reaction solution to separate the layers, and 30 mL of dichloromethane and 80 mL of toluene were added to the aqueous layer to extract the organic layer.

All the above reaction procedures were carried out under the condition that nitrogen gas was continuously introduced into the reaction vessel at a flow rate of 1.1 L/min.

Step 2): Preparation of PEG-dialdehyde

To another reaction vessel, 200 mL of 0.05N hydrochloric acid solution was added, and the previously extracted organic layer was added dropwise over 30 minutes. The reaction solution was stirred at room temperature for 30 minutes and then adjusted to pH 6 using 5% sodium bicarbonate solution. 100 mL of dichloromethane was added to the reaction solution to extract the organic layer, and then sodium sulfate was added to the organic layer and stirred for 30 minutes. The reaction solution was filtered and the filtrate was concentrated under reduced pressure. The concentrate was dissolved in 8 mL of dichloromethane and 200 mL of methyl t-butyl ether was added dropwise over 20 minutes. The resulting crystals were filtered, washed with methyl t-butyl ether, and dried by nitrogen at room temperature to obtain 2.98 g (yield: 30.0%) of the target compound PEG-dialdehyde.

Terminal activity: 81.4%.

EXAMPLE 7

Preparation of PEG-dialdehyde

The same procedure as in Example 6 was repeated to obtain 3.67 g (yield: 37%) of PEG-dialdehyde, except that 0.98 g of sodium ethoxide was used as the metal base.

Terminal activity: 77.8%.

EXAMPLE 8

Preparation of PEG-dialdehyde

The same procedure as in Example 6 was repeated to obtain 2.98 g (yield: 30%) of PEG-dialdehyde, except that 1.38 g of sodium t-butoxide was used as the metal base.

Terminal activity: 81.7%.

EXAMPLE 9

Preparation of PEG-dialdehyde

The same procedure as in Example 6 was repeated to obtain 3.37 g (yield: 34%) of PEG-dialdehyde, except that 1.60 g of potassium t-butoxide was used as the metal base.

Terminal activity: 81.7%.

EXAMPLE 10

Preparation of PEG-dialdehyde

The same procedure as in Example 6 was repeated to obtain 4.68 g (yield: 48%) of PEG-dialdehyde, except that 1.58 g of sodium t-pentoxide was used as the metal base.

Terminal activity: 85.8%.

EXAMPLE 11

Preparation of PEG-dialdehyde

The same procedure as in Example 6 was repeated to obtain 3.47 g (yield: 35%) of PEG-dialdehyde, except that 8.4 mL of potassium t-pentoxide (1.7M toluene solution) was used as the metal base.

Terminal activity: 82.3%.

EXAMPLE 12

Preparation of PEG-dialdehyde

The same procedure as in Example 6 was repeated to obtain 4.36 g (yield: 44%) of PEG-dialdehyde, except that 0.58 g of 60% sodium hydride was used as the metal base.

Terminal activity: 81.9%.

EXAMPLE 13

Preparation of PEG-dialdehyde

Step 1): Preparation of PEG-diethyl Acetal

Nitrogen gas was continuously introduced into two 500 mL reaction vessels, and these reaction vessels were flame dried to remove moisture.

To one of the reaction vessels, 20 mL of toluene and 2.24 mL of 3,3-diethoxy-1-propanol were charged. Thereafter, 0.79 g of sodium t-pentoxide was added and the temperature was raised to 50° C., and the solution was activated by stirring for 1 hour.

To the other reaction vessel, 5 g of PEG-Ms obtained in Preparation Example 1 and 20 mL of toluene were added, and the previously activated solution was added dropwise over 1 hour and then stirred at room temperature for 2 hours. 15 mL of water was added to the reaction solution to separate the layers, and 15 mL of dichloromethane and 40 mL of toluene were added to the aqueous layer to extract the organic layer.

All the above reaction procedures were carried out under the condition that nitrogen gas was continuously introduced into the reaction vessel at a flow rate of 0.56 L/min.

Step 2): Preparation of PEG-dialdehyde

To another reaction vessel, 100 mL of 0.05N hydrochloric acid solution was added, and the previously extracted organic layer was added dropwise over 30 minutes. The reaction solution was stirred at room temperature for 30 minutes and then adjusted to pH 6 using 5% sodium bicarbonate solution. 50 mL of dichloromethane was added to the reaction solution to extract the organic layer, and then sodium sulfate was added to the organic layer and stirred for 30 minutes. The reaction solution was filtered and the filtrate was concentrated under reduced pressure. The concentrate was dissolved in 4 mL of dichloromethane and 100 mL of methyl t-butyl ether was added dropwise over 20 minutes. The resulting crystals were filtered, washed with methyl t-butyl ether, and dried by nitrogen at room temperature to obtain 1.80 g (yield: 36%) of the target compound PEG-dialdehyde.

Terminal activity: 83.7%.

EXAMPLE 14

Preparation of PEG-dialdehyde

The same procedure as in Example 13 was repeated to obtain 1.93 g (yield: 39%) of PEG-dialdehyde, except that the flow of nitrogen gas was adjusted to 1.1 L/min and 5 mL of toluene was further added to the activated solution.

Terminal activity: 86.4%.

EXAMPLE 15

Preparation of PEG-dialdehyde

The same procedure as in Example 13 was repeated to obtain 1.88 g (yield: 38%) of PEG-dialdehyde, except that the flow of nitrogen gas was adjusted to 2.8 L/min and 13 mL of toluene was further added to the activated solution.

Terminal activity: 82.1%.

EXAMPLE 16

Preparation of PEG-dialdehyde

The same procedure as in Example 13 was repeated to obtain 2.03 g (yield: 41%) of PEG-dialdehyde, except that the flow of nitrogen gas was adjusted to 3.7 L/min and 18 mL of toluene was further added to the activated solution.

Terminal activity: 81.4%.

EXAMPLE 17

Preparation of PEG-dialdehyde

The same procedure as in Example 5 was repeated to obtain 4.6 g (yield: 47%) of PEG-dialdehyde, except for using argon gas instead of nitrogen gas as an inert gas.

Terminal activity: 83.1%.

EXAMPLE 18

Preparation of PEG-dialdehyde

The same procedure as in Example 5 was repeated to obtain 4.3 g (yield: 44%) of PEG-dialdehyde, except for using helium gas instead of nitrogen gas as an inert gas.

Terminal activity: 82.4%.

Comparative Example 1

Preparation of PEG-dialdehyde

The same procedure as in Example 6 was repeated, under the condition that no nitrogen gas was introduced into the reaction vessel, to obtain 2.38 g (yield: 24%) of PEG-dialdehyde.

Terminal activity: 13.0%.

Comparative Example 2

Preparation of PEG-dialdehyde

The same procedure as in Example 7 was repeated, under the condition that no nitrogen gas was introduced into the reaction vessel, to obtain 2.68 g (yield: 27%) of PEG-dialdehyde.

Terminal activity: 33.6%.

Comparative Example 3

Preparation of PEG-dialdehyde

The same procedure as in Example 8 was repeated, under the condition that no nitrogen gas was introduced into the reaction vessel, to obtain 2.38 g (yield: 24%) of PEG-dialdehyde.

Terminal activity: 33.9%.

Comparative Example 4

Preparation of PEG-dialdehyde

The same procedure as in Example 9 was repeated, under the condition that no nitrogen gas was introduced into the reaction vessel, to obtain 3.18 g (yield: 32%) of PEG-dialdehyde.

Terminal activity: 69.5%.

Comparative Example 5

Preparation of PEG-dialdehyde

The same procedure as in Example 10 was repeated, under the condition that no nitrogen gas was introduced into the reaction vessel, to obtain 2.88 g (yield: 29%) of PEG-dialdehyde.

Terminal activity: 49.1%.

Comparative Example 6

Preparation of PEG-dialdehyde

The same procedure as in Example 11 was repeated, under the condition that no nitrogen gas was introduced into the reaction vessel, to obtain 3.37 g (yield: 34%) of PEG-dialdehyde.

Terminal activity: 69.8%.

Comparative Example 7

Preparation of PEG-dialdehyde

The same procedure as in Example 12 was repeated, under the condition that no nitrogen gas was introduced into the reaction vessel, to obtain 3.18 g (yield: 32%) of PEG-dialdehyde.

Terminal activity: 68.0%.

Comparative Example 8

Preparation of PEG-dialdehyde

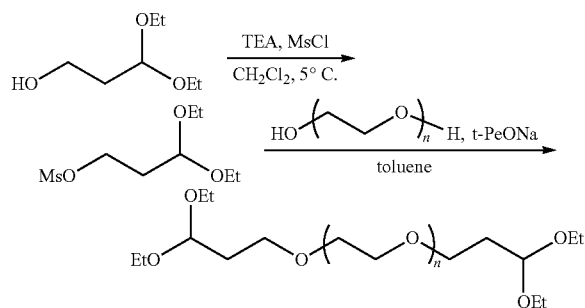

Step 1): Preparation of Diethoxypropyl Methanesulfonate

To the reaction vessel, 1.69 g of 3,3-diethoxy-1-propanol and 17 mL of dichloromethane were charged. While keeping the reaction temperature below 10° C., 1.9 mL of triethylamine and 1.06 mL of methanesulfonyl chloride were added, and the mixture was stirred at 5° C. for 1 hour. To the reaction solution, 20 mL of toluene and 2.24 mL of 3,3-diethoxy-1-propanol were added. When the reaction was completed, 50 mL of water was added, and the mixture was stirred for 5 minutes. After extracting the organic layer, 50 mL of dichloromethane was further added to the aqueous layer to further extract the organic layer. The organic layers were combined, washed with 50 mL of distilled water, dried over magnesium sulfate, filtered, and the filtrate was concentrated under reduced pressure to give diethoxypropyl methanesulfonate $^1$H-NMR (CDCl$_3$, 400 MHz) δ4.65 (t, 1H, J=5.6 Hz), 4.32 (t, 2H, J=5.6 Hz), 3.71-3.64 (m, 2H), 3.56-3.48 (m, 2H), 3.01 (s, 3H), 2.07-2.03 (m, 2H), 1.21 (t, 6H, J=7.2 Hz), Step 2): Preparation of PEG-diethyl Acetal Nitrogen gas was continuously introduced into two reaction vessels, and these reaction vessels were flame dried to remove moisture.

To one of the reaction vessels, 40 mL of toluene and 10 g of polyethylene glycol were charged. Thereafter, 0.70 g of sodium t-pentoxide was added and the temperature was raised to 50° C., and the solution was activated by stirring for 1 hour and cooled to room temperature.

To the other reaction vessel, 2.7 g of diethoxypropyl methanesulfonate prepared in step 1) above and 40 mL of toluene were added, and the previously activated solution was added dropwise over 1 hour and then stirred at room temperature for 2 hours.

All the above reaction procedures were carried out under the condition that nitrogen gas was continuously introduced into the reaction vessel.

As a result of TLC, it was confirmed that diethoxypropyl methanesulfonate was disappeared, but the reaction was proceeded only at a rate of about 30%. The reason why the reaction was not completed as described above seems to be that the intermediate diethoxypropyl methanesulfonate was unstable and thus decomposed.

Comparative Example 9

Preparation of PEG-dialdehyde

The same procedure as in Example 13 was repeated, under the condition that no nitrogen gas was introduced into the reaction vessel, to obtain 1.49 g (yield: 30%) of PEG-dialdehyde.

Terminal activity: 50.1%.

Experimental Example 1

Analysis of Yield and Terminal Activity Depending on Treatment Conditions

The tendency of yield and terminal activity of PEG-dialdehydes prepared in the above Examples and Comparative Examples according to the production conditions were analyzed as follows:

(1) Analysis of Changes in Terminal Activity Depending on Inert Atmosphere During Activation The present invention is carried out in an inert atmosphere when activated, and table 1 below compares and analyzes terminal activity of PEG-dialdehyde which is finally obtained in the presence or absence of inert atmosphere

TABLE 1

| | | Terminal activity (%) | |
| --- | --- | --- | --- |
| Item | Metal base | Use of nitrogen (Example) | Non-use of nitrogen (Comparative Example) |
| Example 6/ Comparative Example 1 | Sodium methoxide | 81.4 | 13.0 |
| Example 7/ Comparative Example 2 | Sodium ethoxide | 77.8 | 33.6 |
| Example 8/ Comparative Example 3 | Sodium t-butoxide | 81.7 | 33.9 |
| Example 9/ Comparative Example 4 | Potassium t-butoxide | 81.7 | 69.5 |
| Example 10/ Comparative Example 5 | Sodium t-pentoxide | 85.8 | 49.1 |
| Example 11/ Comparative Example 6 | Potassium t-pentoxide | 82.3 | 69.8 |
| Example 12/ Comparative Example 7 | Sodium hydride | 81.9 | 68.0 |

Referring to table 1, it can be seen that only when the activation is carried out in a nitrogen atmosphere, it is possible to produce PEG-dialdehyde with excellent terminal activity.

(2) Analysis of Changes in Yield and Terminal Activity Depending on the kind of Inert Gas During Activation Table 2 below compares yield and terminal activity depending on the type of gas in the inert atmosphere.

TABLE 2

| Item | Inert gas | Yield (%) | Terminal activity (%) |
| --- | --- | --- | --- |
| Example 5 | Nitrogen | 48 | 85.8 |
| Example 17 | Argon | 47 | 83.1 |
| Example 18 | Helium | 44 | 82.4 |
| Comparative Example 5 | X | 29 | 49.1 |

Referring to table 2, it can be seen that when the inert gas was used during the activation, terminal activity is almost doubled and has no significant difference depending on the type of inert gas, but when nitrogen is used, it is more advantageous in terms of yield and terminal activity.

Analysis of Changes in Yield and Terminal Activity Depending on the Flow Rate of Inert Gas During Activation Table 3 below compares yield and terminal activity depending on the flow rate of the inert gas.

TABLE 3

| Item | Flow rate of $N_2$ (L/min) | Amount of Solution remaining after activation (mL) | Yield (%) | Terminal activity (%) |
|---|---|---|---|---|
| Comparative Example 9 | 0 | 23 | 30 | 50.1 |
| Example 13 | 0.56 | 23 | 36 | 83.7 |
| Example 14 | 1.1 | 15 | 39 | 86.4 |
| Example 15 | 2.8 | 7 | 38 | 82.1 |
| Example 16 | 3.7 | 2 | 41 | 81.4 |

Referring to table 3, it can be seen that when the activation is carried out in an inert atmosphere, PEG-dialdehyde with high terminal activity can be obtained. In that case, referring to the results depending on the flow rate of the inert gas, it can be seen that PEG-dialdehyde with high terminal activity can be produced at a flow rate of 1.1 L/min.

(4) Purification Treatment after Pegylation

There was a difference in yield and terminal activity depending on the separation and purification method of PEG-diethyl acetal prepared after the pegylation of step 1), and the results are shown in table 4 below.

TABLE 4

| Item | Metal base | Separation and purification method | Terminal activity (%) |
|---|---|---|---|
| Example 1 | Potassium t-butoxide | Extraction-concentration-crystallization | 66.8 |
| Example 2 | Potassium t-butoxide | Extraction-concentration | 73.1 |
| Example 3 | Potassium t-butoxide | Extraction (used in-situ) | 77.1 |
| Example 4 | Sodium t-pentoxide | Extraction (used in-situ) | 82.6 |
| Example 5 | Sodium t-pentoxide | Extraction (used in-situ) | 85.8 |

Referring to table 4, it can be seen that terminal activity of the finally obtained PEG-dialdehyde differs depending on the separation and purification process of PEG-diethyl acetal after the pegylation. Referring to Examples 1 and 2, it can be seen that when performing up to crystallization, terminal activity decreases, and when using the solution separated after the extraction process with the organic layer in the next step (in-situ), it is possible to prepare PEG-dialdehyde with excellent terminal activity.

It can be seen that this tendency was the same even when comparing to Examples 4 and 5 using different kinds of metal bases

The invention claimed is:

1. A method for preparing a polyethylene glycol dialdehyde derivative represented by the following formula 4, comprising
   (1) subjecting a compound of the following formula 2 to an activation treatment with a metal base and then subjecting it to a pegylation with a compound of the following formula 1 to prepare a compound of the following formula 3; and
   (2) subjecting the compound of formula 3 to an acid treatment:

(Formula 1)

(Formula 2)

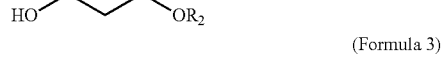
(Formula 3)

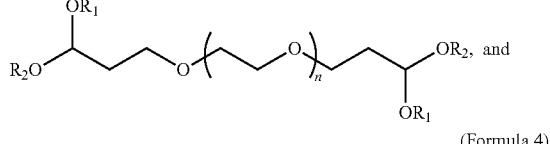

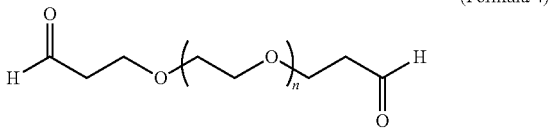
(Formula 4)

wherein Ms is methanesulfonyl, $R_1$ and $R_2$ are the same or different from each other and each independently represents a (C1-C9) alkyl group, and n is an integer of 3 to 2000.

2. The method according to claim 1, characterized in that the metal base is at least one selected from the group consisting of a metal alkoxide and a metal hydride.

3. The method according to claim 2, characterized in that the metal alkoxide is at least one selected from the group consisting of sodium methoxide, sodium ethoxide, sodium t-butoxide, sodium t-pentoxide, potassium t-butoxide and potassium t-pentoxide.

4. The method according to claim 2, characterized in that the metal hydride is sodium hydride.

5. The method according to claim 1, characterized in that the activation treatment is carried out at from 20° C. to 90° C.

6. The method according to claim 1, characterized in that the pegylation is carried out at a temperature of 0° C. to 90° C.

7. The method according to claim 1, characterized in that step (1) is carried out under an inert gas atmosphere or under an inert atmosphere in which an inert gas is continuously introduced.

8. The method according to claim 7, characterized in that the inert atmosphere is formed by introducing at least one inert gas selected from the group consisting of nitrogen, argon and helium.

9. The method according to claim 1, characterized in that step (1) is carried out in at least one solvent selected from the group consisting of toluene, dichloromethane, chloroform, tetrahydrofuran, acetonitrile and 1,4-dioxane.

10. The method according to claim 1, characterized in that the compound of formula 3 prepared in step (1) is applied, as it is, in situ to step (2).

11. The method according to claim 1, characterized in that the acid treatment in step (2) is carried out using at least one acid selected from the group consisting of hydrochloric acid, acetic acid, formic acid, trifluoroacetic acid and phosphoric acid.

12. The method according to claim 1, characterized in that the acid treatment of step (2) is carried out at a temperature between 0° C. and 50° C.

13. The method according to claim 1, characterized in that step (2) is carried out in at least one solvent selected from the group consisting of water, methanol, ethanol, propanol and t-butanol.

14. The method according to claim 1, characterized in that the compound of formula 1 is prepared by reacting polyethylene glycol (PEG) and methanesulfonyl halide (halide=Cl, Br, or F) in the presence of base.

15. The method according to claim 14, characterized in that the base is at least one selected from the group consisting of triethylamine and tributylamine.

* * * * *